United States Patent
Govari et al.

(10) Patent No.: US 10,682,175 B2
(45) Date of Patent: Jun. 16, 2020

(54) USING CATHETER POSITION AND TEMPERATURE MEASUREMENT TO DETECT MOVEMENT FROM ABLATION POINT

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 34 days.

(21) Appl. No.: 14/072,885

(22) Filed: Nov. 6, 2013

(65) Prior Publication Data

US 2015/0126995 A1    May 7, 2015

(51) Int. Cl.
*A61B 18/14*     (2006.01)
*A61B 18/00*     (2006.01)
*A61B 90/00*     (2016.01)

(52) U.S. Cl.
CPC ............ *A61B 18/1492* (2013.01); *A61B 2018/00589* (2013.01); *A61B 2018/00797* (2013.01); *A61B 2018/00898* (2013.01); *A61B 2090/065* (2016.02)

(58) Field of Classification Search
CPC .......... A61B 2018/00714; A61B 2018/00815; A61B 2018/00791; A61B 2018/00799; A61B 2018/00904; A61B 2018/00797
See application file for complete search history.

(56) References Cited

U.S. PATENT DOCUMENTS

| | | | |
|---|---|---|---|
| 5,897,552 | A | 4/1999 | Edwards et al. |
| 6,049,737 | A * | 4/2000 | Simpson ............ A61B 18/1492 607/119 |
| 6,226,542 | B1 | 5/2001 | Reisfeld |
| 6,241,724 | B1 | 6/2001 | Fleischman |
| 6,245,065 | B1 * | 6/2001 | Panescu et al. ................. 606/40 |
| 6,301,496 | B1 | 10/2001 | Reisfeld |
| 6,312,425 | B1 * | 11/2001 | Simpson ............ A61B 18/1492 600/549 |
| 6,695,808 | B2 | 2/2004 | Tom |
| 6,814,733 | B2 | 11/2004 | Schwartz |
| 6,892,091 | B1 | 5/2005 | Ben Haim |

(Continued)

OTHER PUBLICATIONS

U.S. Appl. No. 13/589,347, filed Aug. 20, 2012.

(Continued)

*Primary Examiner* — Michael F Peffley
*Assistant Examiner* — Bo Ouyang

(57) ABSTRACT

Ablation is carried out by bringing a probe into contact with a target tissue. The probe has a plurality of temperature sensors and an ablation electrode on its distal portion. The temperature sensors are distributed circumferentially about the longitudinal axis such that the probe has an omnidirectional temperature sensitivity. After verifying that contact exists between the probe and the target tissue, and while applying energy through the ablation electrode data from the temperature sensors is repetitively recorded. Thereafter, responsively to detection of a drop in temperature with respect to the baseline temperature level, it is concluded that a loss of contact between the probe and the target tissue has occurred. The operator is thereupon alerted.

26 Claims, 3 Drawing Sheets

(56) References Cited

U.S. PATENT DOCUMENTS

| | | | |
|---|---|---|---|
| 6,915,149 | B2 | 7/2005 | Ben Haim |
| 6,997,924 | B2 | 2/2006 | Schwartz |
| 7,156,816 | B2 | 1/2007 | Schwartz |
| 7,536,218 | B2 | 5/2009 | Govari |
| 7,756,576 | B2 | 7/2010 | Levin |
| 9,445,725 | B2 * | 9/2016 | Govari .................... A61B 5/01 |
| 2003/0199863 | A1 | 10/2003 | Swanson et al. |
| 2007/0083194 | A1 * | 4/2007 | Kunis et al. .................... 606/41 |
| 2007/0100332 | A1 | 5/2007 | Paul |
| 2008/0161797 | A1 * | 7/2008 | Wang ................ A61B 18/1492 606/41 |
| 2008/0275465 | A1 | 11/2008 | Paul |
| 2008/0281310 | A1 * | 11/2008 | Dunning ................ A61B 18/16 606/32 |
| 2008/0288038 | A1 | 11/2008 | Paul |
| 2008/0300588 | A1 * | 12/2008 | Groth et al. .................... 606/34 |
| 2009/0093811 | A1 * | 4/2009 | Koblish ............. A61B 18/1492 606/41 |
| 2009/0138007 | A1 | 5/2009 | Govari |
| 2010/0069921 | A1 * | 3/2010 | Miller et al. .................. 606/130 |
| 2010/0168738 | A1 | 7/2010 | Schneider et al. |
| 2011/0264011 | A1 | 10/2011 | Wu et al. |
| 2012/0136346 | A1 * | 5/2012 | Condie ............. A61B 18/1206 606/33 |
| 2012/0157804 | A1 * | 6/2012 | Rogers et al. ................ 600/345 |
| 2013/0204240 | A1 | 8/2013 | McCarthy et al. |

OTHER PUBLICATIONS

U.S. Appl. No. 13/716,578, filed Dec. 17, 2012.
U.S. Appl. No. 13/343,024, filed on Jan. 4, 2012.
European Search Report dated Mar. 3, 2015 for corresponding Application No. EP14191923.
European Exam Report dated May 3, 2016 from corresponding European Patent Application No. 14191923.3.

* cited by examiner

USING CATHETER POSITION AND TEMPERATURE MEASUREMENT TO DETECT MOVEMENT FROM ABLATION POINT

BACKGROUND OF THE INVENTION

Field of the Invention

This invention relates to tissue ablation systems. More particularly, this invention relates to monitoring of contact between an invasive probe and tissue within the body.

Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating such arrhythmias include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey radiofrequency (RF) energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact is sensitive to changes in the impedance between the body-surface electrode and the skin.

U.S. Patent Application Publication Nos. 2008/0288038 and 2008/0275465, both by Sauarav et al., which are herein incorporated by reference, describe an electrode catheter system, which may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

SUMMARY OF THE INVENTION

During an ablation procedure on the heart, it is important that contact be maintained between the electrode providing the ablation power, and the tissue being ablated. The electrode position may itself be monitored by a system such as the CARTO® 3 System, available from Biosense Webster, Inc., 3333 Diamond Canyon Road, Diamond Bar, Calif. 91765. Nevertheless, monitoring contact with the tissue is difficult because of the heart beating, as well as because of the patient breathing. In many cases, the difficulty of monitoring electrode contact is compounded by the fact that the ablation may be performed at more than one point, for example by the physician moving the catheter to create a linear lesion. In this case, it is important not to leave gaps in the lesion, but also not to ablate too much.

The inventor has observed that with a catheter having an omnidirectional temperature response, e.g., an irrigated catheter with at least 3 proximal and 3 distal thermocouples, the temperature measured by the thermocouples stabilizes during ablation, so long as contact is maintained between the catheter and the tissue. However, if there is loss of contact, such as occurs if the catheter moves away from the point of ablation, there is a drop in temperature.

There is provided according to embodiments of the invention a method of ablation, which is carried out by bringing a probe into contact with a target tissue in a body of a subject. The probe has a longitudinal axis, a plurality of temperature sensors on a distal portion of the probe and an ablation electrode thereon. The temperature sensors are distributed circumferentially about the longitudinal axis on the distal portion. The method is further carried out by verifying that contact exists between the probe and the target tissue, and applying energy through the ablation electrode to ablate the target tissue in the body, and while applying the energy performing the steps of repetitively recording data from the temperature sensors, and establishing a baseline temperature level from the data. The method is further carried out thereafter by detecting, from the data, a drop in temperature with respect to the baseline temperature level, and responsively to the drop in temperature, concluding that a loss of contact between the probe and the target tissue has occurred, and alerting an operator to the loss of contact.

According to an aspect of the method, the plurality of temperature sensors includes at least three temperature sensors.

According to another aspect of the method, the temperature sensors are distributed evenly about the longitudinal axis of the probe.

According to a further aspect of the method, the temperature sensors are arranged as a plurality of arrays of temperature sensors, each of the arrays being circumferentially distributed about the longitudinal axis of the probe.

Still another aspect of the method includes filtering the data to exclude artifacts.

According to an additional aspect of the method, the drop in temperature is at least 10 times greater than the noise level.

One aspect of the method includes detecting from the data a restoration in temperature to the baseline temperature level, and responsively to the restoration in temperature, concluding that a restoration of contact between the probe and the target tissue has occurred, and alerting the operator to the restoration of contact.

According to a further aspect of the method, the probe has an omni-directional temperature response.

There is further provided according to embodiments of the invention an apparatus for catheterization, including a probe adapted for insertion into contact with a target tissue in a body of a subject. The probe has a longitudinal axis, a plurality of temperature sensors on a distal portion of the probe and an ablation electrode thereon. The temperature sensors are distributed circumferentially about the longitudinal axis on the distal portion. The apparatus includes a processor operative for applying energy through the ablation electrode to ablate the target tissue in the body, and while applying energy the processors is operative for repetitively recording data from the temperature sensors, establishing a baseline temperature level from the data. The processors is operative for detecting from the data a drop in temperature with respect to the baseline temperature level, and responsively to the drop in temperature, concluding that a loss of contact between the probe and the target tissue has occurred, and alerting an operator to the loss of contact.

According to one aspect of the apparatus, the plurality of temperature sensors includes at least three temperature sensors.

According to another aspect of the apparatus, the temperature sensors are distributed evenly about the longitudinal axis of the probe.

According to an additional aspect of the apparatus, the temperature sensors are arranged as a plurality of arrays of temperature sensors, each of the arrays being circumferentially distributed about the longitudinal axis of the probe.

According to still another aspect of the apparatus, the processor is operative for filtering the data to exclude artifacts.

According to yet another aspect of the apparatus, the drop in temperature is at least 10 times greater than a noise level.

According to a further aspect of the apparatus, the processor is operative for detecting from the data a restoration in temperature to the baseline temperature level, and responsively to the restoration in temperature, concluding that a restoration of contact between the probe and the target tissue has occurred, and alerting the operator to the restoration of contact.

According to one aspect of the apparatus, the probe has an omni-directional temperature.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

The term "couple" or "coupled" is intended to mean either an indirect or a direct connection. Thus, if a first device is coupled to a second device, that connection may be through a direct connection, or through an indirect connection via other devices and connections, or via inductive or capacitive coupling.

Figure 1:
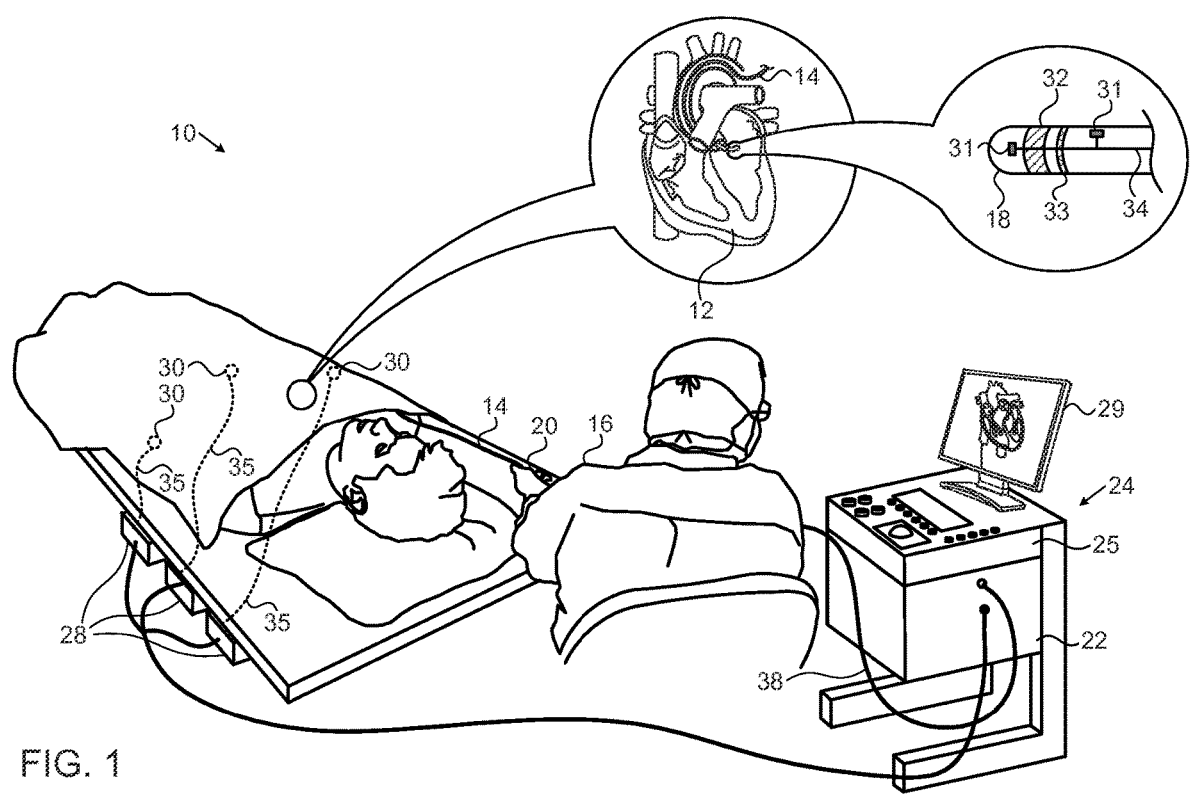
FIG. 1 is a pictorial illustration of a system for performing diagnostic and therapeutic procedures in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with an embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is the above-mentioned CARTO system. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24, are disposed between the ablation electrodes 32 and have connections to the cable 34.

Wire connections 35 link the console 24 with body surface electrodes 30 and other components of a positioning sub-system, which may be incorporated in the console 24 and operated under control of the positioning processor 22. The electrodes 32 and the body surface electrodes 30 may be used to measure tissue impedance at the ablation site as taught in U.S. Pat. No. 7,536,218, issued to Govari et al., which is herein incorporated by reference. Temperature sensors such as thermocouples 31, may be mounted on or near the ablation electrode 32 and optionally or near the sensing electrode 33. The thermocouples 31 are arranged on the catheter 14 in accordance with the principles of the invention, as described in further detail below.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

The positioning subsystem may employ impedance measurement, as taught, for example in U.S. Pat. No. 7,756,576, which is hereby incorporated by reference, and in the above-noted U.S. Pat. No. 7,536,218. Optionally, the positioning subsystem comprises a magnetic position tracking arrangement that determines the position and orientation of the catheter 14 by generating magnetic fields in a predefined working volume and sensing these fields at the catheter, using field-generating coils 28.

As noted above, the catheter 14 is coupled to the console 24, which enables the operator 16 to observe and regulate the functions of the catheter 14. Console 24 typically includes the positioning processor 22, which is preferably a computer with appropriate signal processing circuits. The processor is coupled to a monitor 29. The signal processing circuits typically receive, amplify, filter and digitize signals from the catheter 14, including signals generated by the above-noted sensors and. When a magnetic position tracking arrangement is present, a plurality of location sensing electrodes (not shown) are located distally in the catheter 14. The digitized signals are received and processed by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Figure 2:
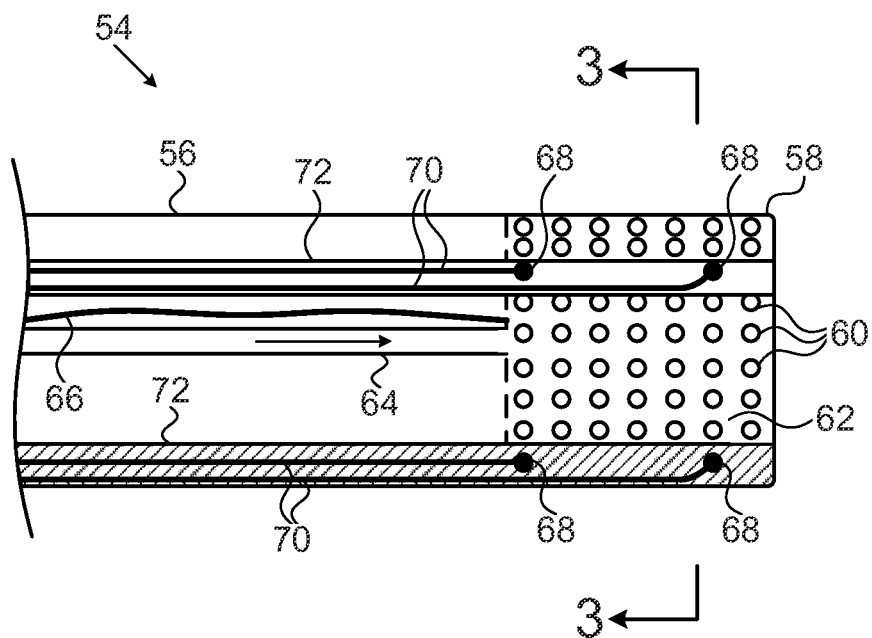
FIG. 2 is a sectional view along the length of a distal segment of a cardiac catheter, in accordance with an embodiment of the invention.

Reference is now made to FIG. 2, which is a sectional view along the length of distal segment 54 of a cardiac catheter having an omnidirectional temperature response (e.g., about the longitudinal axis of the catheter), in accordance with an embodiment of the invention.

An insertion tube 56 extends along the length of the catheter and is connected at its distal end to a conductive cap 58. Typically, the insertion tube 56 comprises a flexible, biocompatible polymer, while the cap 58 comprises a biocompatible metal suitable to serve as an ablation electrode, such as gold or platinum, for example. The cap 58 may be perforated by an array of irrigation apertures 60, which open from the outer surface of the cap into an inner cavity 62. For typical intracardiac ablation applications, the diameter of the cap 58 may be about 2.5 mm, with a wall thickness of about 0.2 mm and apertures 60 of diameter 0.1-0.2 mm. The above dimensions and materials are described by way of example, however, and other suitable materials, with features of larger or smaller dimensions, may similarly be used.

The cavity 62 is in fluid communication with a lumen 64, which runs through the length of the insertion tube 56. The lumen 64 is coupled at its proximal end to an irrigation pump (not shown), and thus conveys irrigation fluid to the cavity 62, from which the fluid flows out through apertures 60. An electrical conductor 66 conveys electrical energy from an RF generator (not shown) through the insertion tube 56 to the cap 58, and thus energizes the cap 58 to ablate myocardial tissue with which the cap 58 is in contact. During ablation, the fluid flowing out through apertures 60 irrigates the tissue under treatment.

Temperature sensors 68 are mounted within the cap 58 at locations that are circumferentially arrayed around the distal tip of the catheter, optionally, a plurality of circumferential arrays of temperature sensors may be disposed axially about the cap 58. The temperature sensors are distributed substantially evenly about the circumference of the catheter, i.e., about its longitudinal axis. FIG. 2 shows two arrays of temperature sensors 68. In any case, the temperature sensors 68 are able to sense the temperature at any point along about the circumference of the distal segment 54. Increasing the number of temperature sensors 68 about this circumference improves the angular resolution. However, in medical applications, three sensors, equally distributed about the circumference are sufficient to provide a substantially omnidirectional temperature response with respect to the longitudinal axis. In the example of FIG. 2, cap 58 contains six sensors, with one group in a distal location, close to the tip, and the other group in a slightly more proximal location. This distribution is shown only by way of example, however, and greater or smaller numbers of sensors may be mounted in any suitable locations within the cap 58. Temperature sensors 68 may comprise thermocouples, thermistors, or any other suitable type of miniature temperature sensor. The sensors 68 are connected by leads 70 running through the length of insertion tube 56 to provide temperature signals to monitoring circuitry (not shown).

Figure 3:
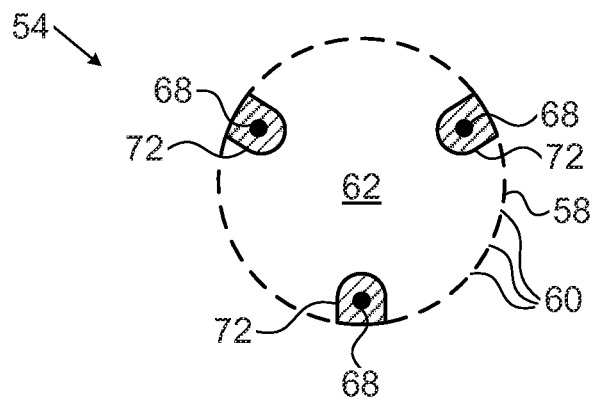
FIG. 3 is a sectional view through line 3-3 of FIG. 2, in accordance with an embodiment of the invention.

Reference is now made to FIG. 3, which is a schematic sectional view through line 3-3 of FIG. 2, in accordance with an embodiment of the invention. The temperature sensors 68 are mounted within ribs 72 inside the cap 58. The ribs 72 are typically an integral part of the cap 58 and may be made from the same material as the outer surface of the cap 58 or from some other suitable type of metal, which is physically and thermally bonded to the cap 58. The diameter of the ribs may be a few tenths of a millimeter in the present example. The integral construction of the ribs 72 with the cap 58 causes the temperature sensors 68 to be in thermal communication with the outer surface of the cap 58, i.e., the temperature inside the ribs 72 closely tracks the temperature of the outer surface. The ribs 72 are thick enough to thermally insulate the temperature sensors 68 from the irrigation fluid in the cavity 62. As a result, the temperature sensors 68 measure the true temperature of the outer surface of the cap 58, which most accurately reflects the temperature of the tissue with which the cap 58 is in contact.

Typically, the distal segment 54 contains other functional components, which are outside the scope of the present disclosure and are therefore omitted for the sake of simplicity. For example, the distal segment 54 may contain steering wires, as well as sensors of other types, such as a position sensor and/or a contact force sensor. A catheter containing sensors of these sorts is described, for example, in U.S. Patent Application Publication 2009/0138007, whose disclosure is incorporated herein by reference.

Catheters of the kind described with reference to FIG. 2 and FIG. 3 are described in further detail in commonly assigned copending application Ser. No. 13/716,578, which is herein incorporated by reference.

Operation.

Figure 4:
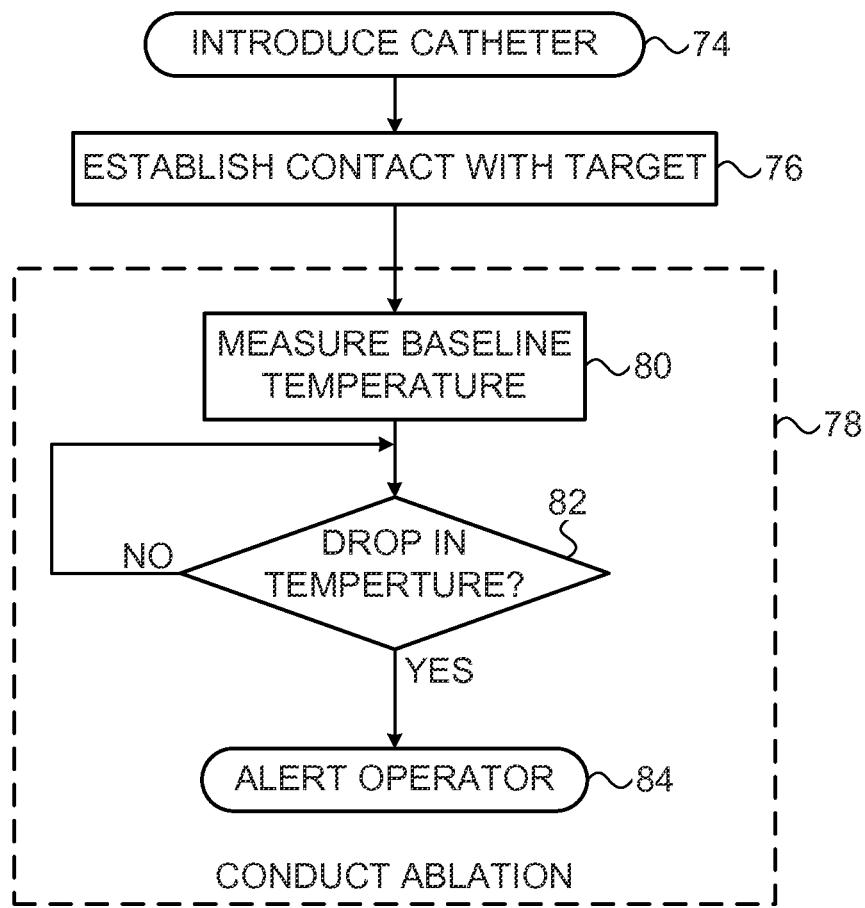
FIG. 4 is a flow chart of a method for monitoring contact between a cardiac catheter and an ablation point, in accordance with an embodiment of the invention.

Reference is now made to FIG. 4, which is a flow chart of a method for monitoring contact between a cardiac catheter and an ablation point, in accordance with an embodiment of the invention.

At initial step 74, a cardiac catheter is introduced into the heart of a subject using well-known methods.

Next, at step 76 contact is established between the ablation electrode of the catheter and the target. This may be accomplished by any known method, e.g., any of the methods described above and the methods taught in application Ser. No. 13/343,024, entitled "Contact Assessment Based on Phase Measurement" and application Ser. No. 13/589,347, entitled "Machine Learning in Determining Catheter Electrode Contact". Both Applications are commonly assigned herewith and are herein incorporated by reference.

Next, at step 78 ablation of the target is conducted. Step 78 includes the following steps:

At step 80, a baseline temperature is measured using signals from the temperature sensors 68. The data is filtered to remove artifacts caused by respiration, patient motion, and movements of the catheter not affecting the contact state, using well-known methods and circuitry. As the catheter has an omnidirectional temperature response, the measured temperature in the environment of the temperature sensors 68 is essentially indifferent to the attitude of the distal segment of the catheter with respect to the ablation target.

Next, at delay step 82, a significant drop in temperature (approximately 10 times the noise level) with respect to the baseline that was established in step 80 is awaited. The magnitude of the drop is dependent on variables such as the ablation power, the number of ablation electrodes being concurrently employed, and the flow rate of irrigation fluid. Delay step 82 could be performed by a human operator, in which case the temperature is shown on a monitor. However, delay step 82 is preferably performed automatically, using conventional temperature monitoring circuitry.

When a determination in the performance of delay step 82 indicates that a drop in temperature has occurred, loss of contact between the catheter and the target tissue is indicated. The operator is alerted at final step 84.

Figure 5:
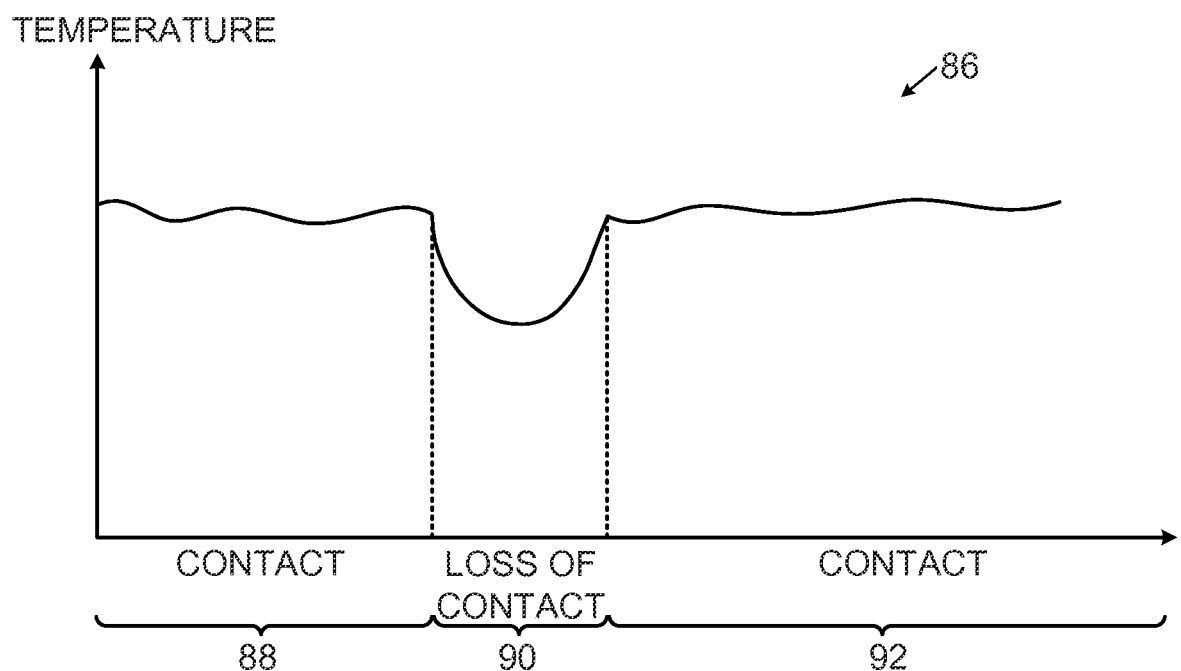
FIG. 5 is a graph of time-varying temperatures measured by the temperature sensors shown in FIG. 2 during a procedure performed in accordance with an embodiment of the invention.

Reference is now made to FIG. 5, which is a plot 86 of temperature that would be measured by the temperature sensors 68 (FIG. 2) during a typical ablation operation, performed in accordance with the procedure described with reference to FIG. 4. It is assumed that contact between the catheter and the target has previously been established, for example, using the above-noted methods. The ablator is then energized throughout the other time intervals displayed on the horizontal axis of the plot 86. During an interval 88, contact is indicated between the catheter and the target by maintenance of an initial baseline temperature. During an interval 90, loss of contact is indicated by a drop in temperature. However, this condition may have been corrected as shown by a subsequent rise in temperature during the latter portion of the interval 90. Then, during an interval 92, contact has been reestablished, as shown by return of the temperature to the baseline level of the interval 88.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of verifying tissue contact during ablation, comprising the steps of:

providing a probe having a distal tip and adapted for insertion into contact with a target tissue in a body of a subject, the probe having a longitudinal axis and a conductive cap at the distal tip of the probe, the conductive cap adapted for use as an ablation electrode, the conductive cap having an outer surface and an inner surface, the inner surface forming a cavity, the outer surface being made entirely from a conductive biocompatible metal and a plurality of temperature sensors mounted within raised ribs along the inner surface of the conductive cap, the raised ribs being configured to project radially inward toward the longitudinal axis relative to the adjacent inner surface, the plurality of temperature sensors being circumferentially arrayed around the distal tip of the probe and configured to be in thermal communication with the outer surface of the conductive cap such that the temperature inside the raised ribs closely tracks the temperature of the outer surface of the conductive cap, and have an omnidirectional temperature response where the measured temperature in the environment of the temperature sensors is indifferent to the attitude of the distal tip with respect to the target tissue in the body;
bringing the probe into contact with a target tissue in a body of a subject;
verifying that contact exists between the probe and the target tissue; and
applying energy through the ablation electrode to ablate the target tissue in the body, and while applying energy performing the steps of:
repetitively recording data from the temperature sensors;
filtering the data to remove artifacts caused by movements not affecting the contact state;
establishing a baseline temperature level from the data;
thereafter from the data detecting a drop in temperature with respect to the baseline temperature level;
responsively to the drop in temperature, concluding that a loss of contact between the probe and the target tissue has occurred;
alerting an operator to the loss of contact; and
reestablishing contact.

2. The method according to claim 1, wherein the plurality of temperature sensors comprises at least three temperature sensors.

3. The method according to claim 2, wherein the temperature sensors are distributed evenly about the longitudinal axis of the probe.

4. The method according to claim 1, wherein the plurality of temperature sensors comprises a plurality of arrays of temperature sensors, each of the arrays being circumferentially distributed about the longitudinal axis of the probe.

5. The method according to claim 1, further comprising the step of filtering the data to exclude artifacts.

6. The method according to claim 1, wherein the drop in temperature is at least 10 times greater than a noise level.

7. The method according to claim 1, further comprising the steps of:
detecting from the data a restoration in temperature to the baseline temperature level;
responsively to the restoration in temperature, concluding that a restoration of contact between the probe and the target tissue has occurred; and
alerting the operator to the restoration of contact.

8. The method according to claim 1, wherein the probe has an omni-directional temperature response about the longitudinal axis.

9. An apparatus for verifying tissue contact during catheterization, comprising:
a probe having a distal tip and adapted for insertion into contact with a target tissue in a body of a subject, the probe having a longitudinal axis and a conductive cap at the distal tip of the probe, the conductive cap adapted for use as an ablation electrode and having an outer surface and an inner surface, the inner surface forming a cavity, the outer surface being made entirely from a conductive biocompatible metal, and a plurality of temperature sensors mounted within raised ribs along the inner surface of the conductive cap, the raised ribs being configured to project radially inward toward the longitudinal axis relative to the adjacent inner surface, the plurality of temperature sensors being circumferentially arrayed around the distal tip of the probe and in thermal communication with the outer surface of the conductive cap such that the temperature of the temperature sensor closely tracks the temperature of the outer surface of the conductive cap, and have an omnidirectional temperature response where the measured temperature in the environment of the temperature sensors is indifferent to the attitude of the distal tip with respect to the target tissue in the body;
a processor operative for applying energy through the ablation electrode to ablate the target tissue in the body, and while applying energy performing the steps of:
repetitively recording data from the temperature sensors;
filtering the data to remove artifacts caused by movements not affecting the contact state;
establishing a baseline temperature level from the data;
thereafter from the data detecting a drop in temperature with respect to the baseline temperature level;
responsively to the drop in temperature, concluding that a loss of contact between the probe and the target tissue has occurred;
alerting an operator to the loss of contact; and
reestablishing contact.

10. The apparatus according to claim 9, wherein the plurality of temperature sensors comprises at least three temperature sensors.

11. The apparatus according to claim 10, wherein the temperature sensors are distributed evenly about the longitudinal axis of the probe.

12. The apparatus according to claim 9, wherein the plurality of temperature sensors comprises a plurality of arrays of temperature sensors, each of the arrays being circumferentially distributed about the longitudinal axis of the probe.

13. The apparatus according to claim 9, wherein the processor is operative for filtering the data to exclude artifacts.

14. The apparatus according to claim 9, wherein the drop in temperature is at least 10 times greater than a noise level.

15. The apparatus according to claim 9, wherein the processor is operative for:
detecting from the data a restoration in temperature to the baseline temperature level;
responsively to the restoration in temperature, concluding that a restoration of contact between the probe and the target tissue has occurred; and
alerting the operator to the restoration of contact.

16. The apparatus according to claim 9, wherein the probe has an omni-directional temperature response about the longitudinal axis.

17. An apparatus for verifying tissue contact during catheterization, comprising:
a probe adapted for insertion into contact with a target tissue in a body of a subject, the probe having a longitudinal axis and a conductive cap at a distal end of the probe, the conductive cap adapted for use as an ablation electrode, the conductive cap having a proximal end a distal end, an outer surface and an inner surface, the inner surface forming a cavity, the outer surface being made entirely from a conductive biocompatible metal from the distal end to the proximal end, and a plurality of circumferential arrays of temperature sensors mounted within raised ribs along the inner surface of the conductive cap, the raised ribs being configured to project radially inward toward the longitudinal axis relative to the adjacent inner surface, one of the arrays of temperature sensors being arranged at the proximal end of the conductive cap and another one of the arrays of temperature sensors being arranged at the distal end of the conductive cap, the arrays of temperature sensors being configured to have an omnidirectional temperature response where the measured temperature in the environment of the temperature sensors is indifferent to the attitude of the distal tip with respect to the target tissue in the body;

a processor operative for applying energy through the ablation electrode to ablate the target tissue in the body, and while applying energy performing the steps of:

repetitively recording data from the temperature sensors;

filtering the data to remove artifacts caused by movements not affecting the contact state;

establishing a baseline temperature level from the data;

thereafter from the data detecting a drop in temperature with respect to the baseline temperature level;

responsively to the drop in temperature, concluding that a loss of contact between the probe and the target tissue has occurred;

alerting an operator to the loss of contact; and reestablishing contact.

18. The apparatus according to claim 17, wherein each of the circumferential arrays of temperature sensors comprises at least three temperature sensors.

19. The apparatus according to claim 18, wherein the temperature sensors are distributed evenly about the longitudinal axis of the probe.

20. The apparatus according to claim 17, wherein the drop in temperature is at least 10 times greater than a noise level.

21. The apparatus according to claim 17, wherein the processor is operative for:

detecting from the data a restoration in temperature to the baseline temperature level;

responsively to the restoration in temperature, concluding that a restoration of contact between the probe and the target tissue has occurred; and alerting the operator to the restoration of contact.

22. The apparatus according to claim 17, wherein the probe has an omni-directional temperature response about the longitudinal axis.

23. An apparatus for verifying tissue contact during catheterization, comprising:

a probe having a distal tip and adapted for insertion into contact with a target tissue in a body of a subject, the probe having a longitudinal axis and a conductive cap located at the distal tip of the probe, the conductive cap includes an outer surface and an inner surface, the inner surface forming a cavity, the outer surface being made entirely from a conductive biocompatible metal, the inner cavity being in fluid communication with a lumen coupled at its proximal end to irrigation fluid such that the irrigation fluid can be conveyed to the inner cavity, the conductive cap adapted for use as an ablation electrode;

a plurality of temperature sensors mounted within raised ribs along the inner surface of the conductive cap such that the plurality of temperature sensors are circumferentially arrayed around the distal tip of the probe, each raised rib being configured to project radially inward toward the longitudinal axis relative to the adjacent inner surface and be in thermal communication with the outer surface of the cap such that the temperature inside the raised ribs closely tracks the temperature of the outer surface of the conductive cap, and to thermally insulate the temperature sensors from irrigation fluid in the cavity; and a processor operative for applying energy through the ablation electrode to ablate the target tissue in the body, and while applying energy, and while applying energy performing the steps of:

repetitively recording data from the temperature sensors;

filtering the data to remove artifacts caused by movements not affecting the contact state;

establishing a baseline temperature level from the data;

thereafter from the data detecting a drop in temperature with respect to the baseline temperature level;

responsively to the drop in temperature, concluding that a loss of contact between the probe and the target tissue has occurred;

alerting an operator to the loss of contact; and reestablishing contact.

24. The apparatus according to claim 23 wherein the raised ribs are an integral part of the conductive cap.

25. The apparatus according to claim 24 where the raised ribs are made from the same biocompatible conductive metal as the outer surface of the conductive cap.

26. The apparatus according to claim 23 where the raised ribs are made from a different material than the outer surface of the conductive cap but are physically and thermally bonded to the inner surface conductive cap.

* * * * *